United States Patent [19]

Kelly et al.

[11] 4,082,776
[45] Apr. 4, 1978

[54] 6-ALKOXY-4α-HYDROXY-2β-TETRAHYDROPYRANACETIC ACID γ-LACTONES

[75] Inventors: Robert C. Kelly, Kalamazoo; Norman A. Nelson, Galesburg, both of Mich.

[73] Assignee: The Upjohn Company, Kalamazoo, Mich.

[21] Appl. No.: 770,817

[22] Filed: Feb. 22, 1977

Related U.S. Application Data

[62] Division of Ser. No. 676,890, Apr. 14, 1976, Pat. No. 4,020,173.

[51] Int. Cl.$^2$ ............................................. C07D 493/04
[52] U.S. Cl. .................................................. 260/343.6
[58] Field of Search ...................................... 260/343.6

[56] References Cited

U.S. PATENT DOCUMENTS 4,020,173   4/1977   Kelly et al. ...................... 260/343.6

OTHER PUBLICATIONS

Olsen et al., "Chem Abstracts", vol. 54 (1960), pp. 8824–8826.

Primary Examiner—Natalie Trousof
Assistant Examiner—R. W. Ramsuer
Attorney, Agent, or Firm—Robert A. Armitage

[57] ABSTRACT

The present specification provides novel intermediates and novel processes for the synthesis of Thromboxane B$_2$ 11a- homo-11a-oxa-PGF$_{2\alpha}$), its 15-epimer, and various carboxyl derivatives thereof. In particular, there are disclosed various bicyclic tetrahydropyran-containing lactones useful in the above processes, and corresponding acyclic lactones.

2 Claims, No Drawings

6-ALKOXY-4α-HYDROXY-2β-TETRAHYDROPYRANACETIC ACID γ-LACTONES

The present application is a divisional application of Ser. No. 676,890, filed Apr. 14, 1976, now issued as U.S. Pat. No. 4,020,173 on Apr. 26, 1977.

The present invention relates to Thromboxane B₂ and associated intermediates and processes, for which the essential material constituting disclosure therefor is incorporated by reference here from Ser. No. 676,890, filed Apr. 14, 1976, now issued as U.S. Pat. No. 4,020,173 on Apr. 26, 1977.

We claim:

1. A thromboxane intermediate of the formula

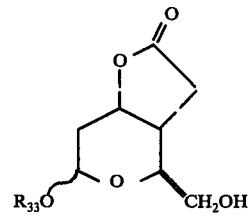

wherein $R_{33}$ is alkyl of one to 5 carbon atoms, inclusive.

2. 6α- or 6β-Methoxy-4α-hydroxy-2β-hydroxymethyl-3α-tetrahydropyranacetic acid γ-lactone, thromboxane intermediates according to claim 1.

* * * * *